United States Patent [19]

Tanaka et al.

[11] Patent Number: 5,662,639
[45] Date of Patent: Sep. 2, 1997

[54] WINGED SANITARY NAPKIN

[75] Inventors: Yoshikazu Tanaka, Kagawa-ken; Takaaki Shimada, Shizuoka-ken; Wataru Yoshimasa, Ehime-ken, all of Japan

[73] Assignee: UNI-Charm Corporation, Ehime-ken, Japan

[21] Appl. No.: 546,257

[22] Filed: Oct. 20, 1995

[30] Foreign Application Priority Data

Oct. 27, 1994 [JP] Japan ................................ 6-263965

[51] Int. Cl.⁶ ........................................... A61F 13/15
[52] U.S. Cl. ..................... 604/387; 604/390; 428/41.8
[58] Field of Search .................................. 604/389, 390, 604/387, 385.1, 386; 428/41.8

[56] References Cited

U.S. PATENT DOCUMENTS

| | | | |
|---|---|---|---|
| 3,688,771 | 9/1972 | Werner | 604/390 |
| 4,900,320 | 2/1990 | McCoy | 604/387 |
| 5,133,704 | 7/1992 | Wheeler | 604/390 |
| 5,201,727 | 4/1993 | Nakanishi et al. | 604/389 |
| 5,569,230 | 10/1996 | Fisher et al. | 604/387 |
| 5,591,521 | 1/1997 | Arakawa et al. | 604/389 |

FOREIGN PATENT DOCUMENTS 6-26833  4/1994  Japan.

*Primary Examiner*—Mark O. Polutta
*Attorney, Agent, or Firm*—Lowe, Price, LeBlanc & Becker

[57] ABSTRACT

A sanitary napkin has a pair of wings extending outward from transversely opposite side edges of the napkin. The wings are folded back onto a top surface of the napkin and provided on lower surfaces of the wings with first and second adhesive zones, respectively. The first and second adhesive zones are covered with a strip of separator having first and second end portions. The first end portion is folded back onto an inner surface of the separator, an outer surface of the folded first end portion being peelably applied to the first adhesive zone, the second end portion being peelably applied to the second adhesive zone.

3 Claims, 2 Drawing Sheets

WINGED SANITARY NAPKIN

BACKGROUND OF THE INVENTION

The present invention relates to a sanitary napkin and more particularly, to a sanitary napkin or a menstruation pad for absorbing menstrual discharge.

Conventional sanitary napkins with a pair of wings generally have an adhesive zone provided on a lower surface of each wing as well as a separator applied onto the adhesive zone. For example, Japanese Utility Model Laid-Open Application No. Hei6-26833 discloses a sanitary napkin wherein, after a pair of wings have been folded back onto a topsheet of the napkin, transversely opposite end portions of a strip of separator are applied to an adhesive zone of each wing.

In the separator of the above-mentioned napkin, a wearer often peels one end portion of the separator off one wing with her one hand and then peels the other end portion of the separator off the other wing with her other hand, when she peels the separator off the wings in their extending direction. Shifting the hand from one end portion to the other end portion of the separator in this manner is troublesome for every wearer. In addition, the end portion of the separator which has been peeled off one wing may often stick again to the wing during operation of shifting the hand from one end portion to the other end portion of the separator and thereby increases troublesomeness.

Accordingly, it is a principal object of this invention to eliminate the conventional troublesomeness.

SUMMARY OF THE INVENTION

The object set forth is achieved, according to the invention, by a sanitary napkin comprising a liquid-permeable topsheet, a liquid-impermeable backsheet, a liquid-absorbent core disposed between the topsheet and backsheet, first and second wings having upper and lower surfaces and extending outward from transversely opposite side edges of the napkin and folded back onto the topsheet above the core respectively, and a separator having outer and inner surfaces and peelably applied to first and second adhesive zones on the lower surfaces of the first and second wings, wherein:

the separator further has first and second end portions, the first end portion being folded back onto the inner surface of the separator, the outer surface of the first end portion being peelably applied to the first adhesive zone, the second end portion of the separator being peelably applied to the second adhesive zone.

In a variant of the invention, the inner surface of the second end portion is peelably applied to the second adhesive zone.

In a further variant of the invention, the second end portion of the separator is folded back onto the inner surface of the separator and the outer surface of the second end portion is peelably applied to the second adhesive zone.

DETAILED DESCRIPTION OF THE EMBODIMENT

A sanitary napkin according to the invention will be explained by the following description of a presently preferred embodiment made in reference with the accompanying drawings.

Figure 1:
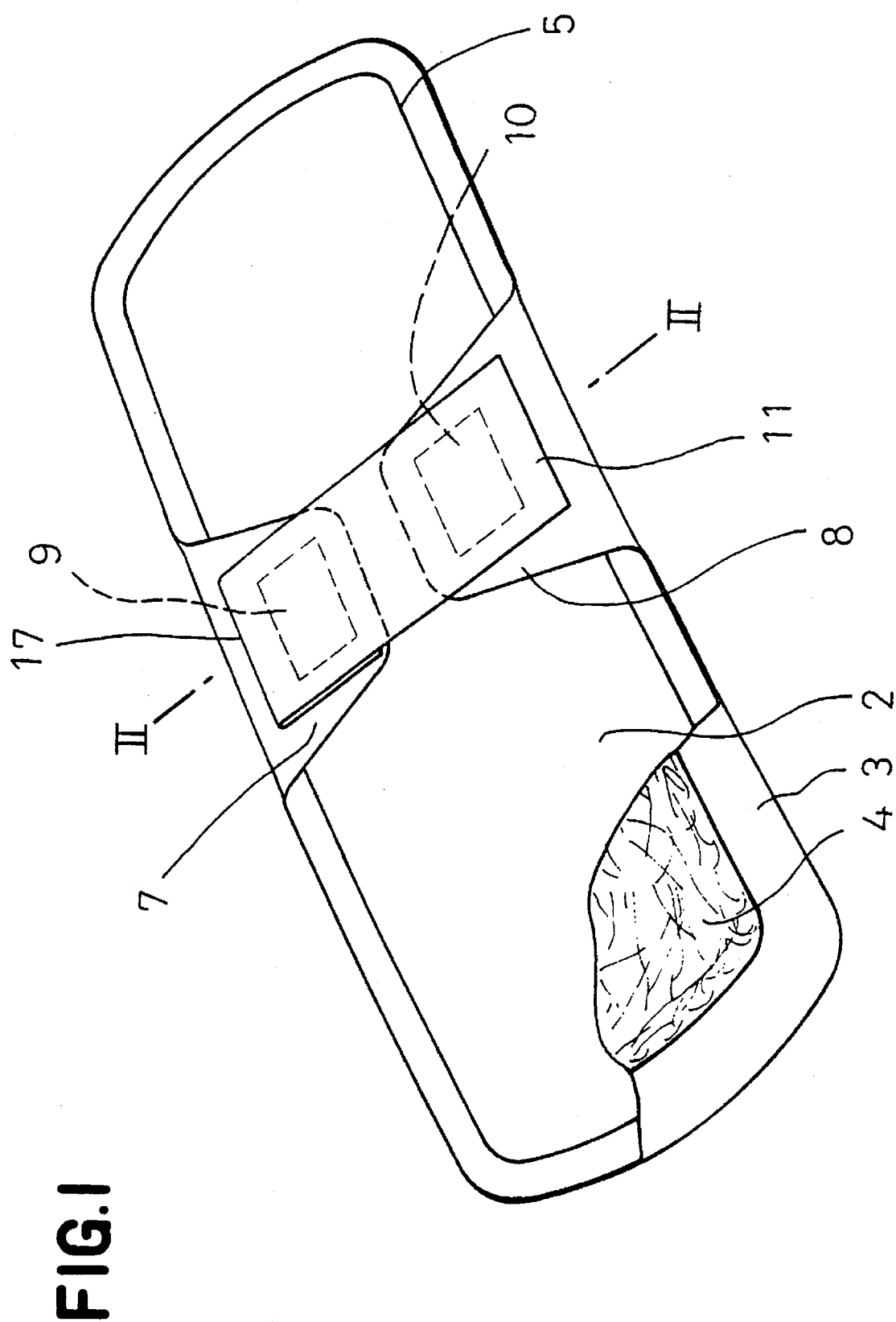
FIG. 1 is a perspective view showing a sanitary napkin as partially broken away.
Figure 2:
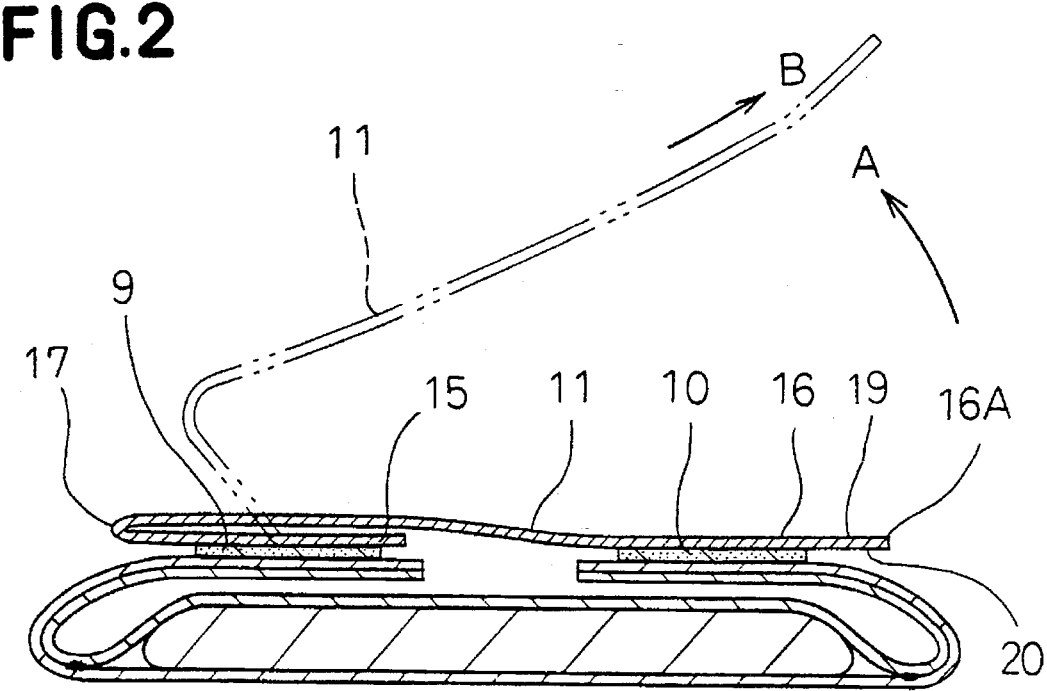
FIG. 2 is a sectional view taken along a line II—II in FIG. 1.

Referring to FIGS. 1 and 2, a sanitary napkin 1 comprises a liquid-permeable topsheet 2, a liquid-impermeable backsheet 3 and a liquid-absorbent core 4 disposed between the topsheet and the backsheet 2, 3, respectively. Portions of the top- and backsheets 2, 3 extending outward beyond a peripheral edge of the core 4 are bonded together by a seal line 5. The topsheet and the backsheet 3 bonded together extend outward from transversely opposite side edges of the napkin 1 at locations slightly aside to a longitudinally forward end of the napkin 1 to define wings 7, 8, respectively. These wings 7, 8 are folded back onto the topsheet 2 and a separator 11 is peelably applied to adhesive zones 9, 10 provided on bottom surfaces of the respective wings 7, 8, i.e., now facing upward as the respective wings have been folded back.

The separator 11 is made of a strip of paper or plastic film or their laminate and has outer and inner surfaces 19, 20 as well as transversely opposite end portions 15, 16. The left end portion 15 is folded back along a fold line 17 to the inner surface 20. The outer surface 19 of the left end portion 15 thus folded is peelably applied to the adhesive zone 9 and the inner surface 20 of the right end portion 16 not folded is peelably applied to the adhesive zone 10 so that an end 16A extends outward beyond the adhesive zone 10. The separator 11 is previously treated with a release agent so as to peel off the adhesive zones 9, 10.

To peel the separator 11 off the wings, the napkin 1 is held with a wearer's one hand and the separator 11 is held at a location adjacent the end 16A with the other hand. First, the separator 11 is pulled up obliquely leftward in the direction as indicated by an arrow 'A' to peel the separator 11 off the adhesive zone 10 as indicated by imaginary lines in FIG. 2. Then the separator 11 is pulled up obliquely rightward in the direction as indicated by an arrow 'B' to peel the separator 11 off the adhesive zone 9. In this manner, the separator 11 can be peeled off the adhesive zones 9, 10 without shifting a wearer's hand from one end portion to the other end portion of the separator 11.

Figure 3:
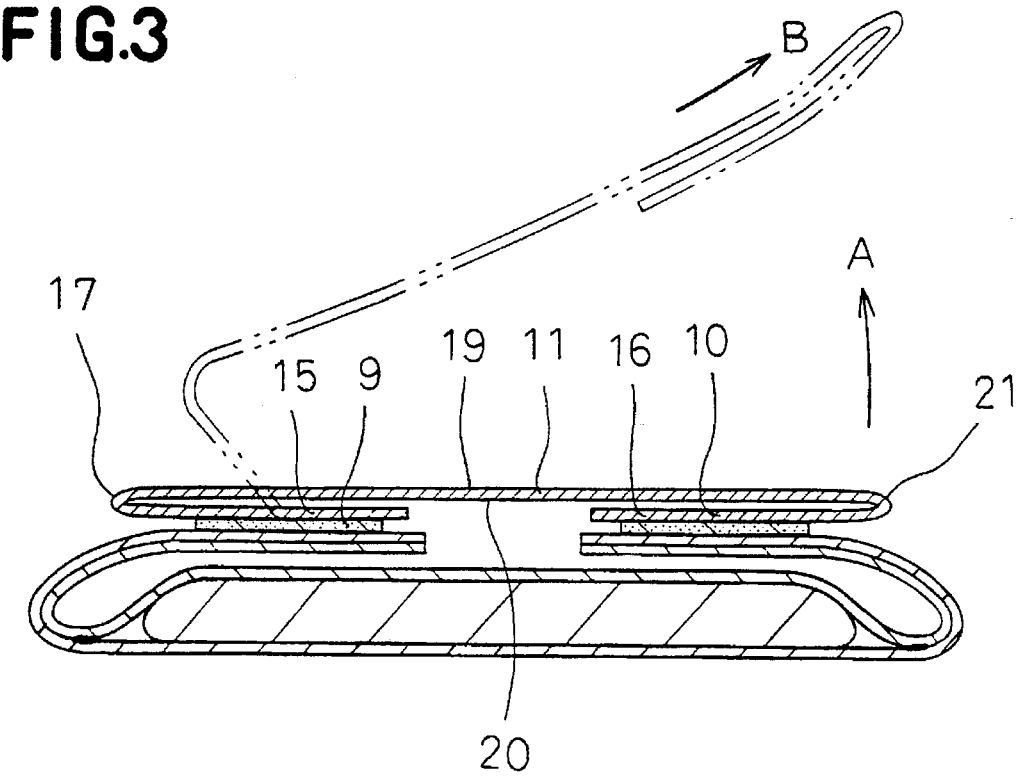
FIG. 3 is a sectional view showing a variant of the sanitary napkin shown by FIG. 1.

Referring to FIG. 3, with this napkin 1, the end portions 15, 16 of the separator 11 are folded back along respective fold lines 17, 21. The outer surface 19 of the end portions 15, 16 thus folded back are peelably applied to the adhesive zones 9, 10 so that the fold lines 17, 21 lie outside the respective adhesive zones 9, 10. To peel the separator 11 off the adhesive zones 9, 10, for example, first the separator 11 is held at the location adjacent the fold line 21 and pulled up obliquely leftward in the direction as indicated by an arrow 'A' to peel the separator 11 off the adhesive zone 10 as indicated by imaginary lines. Then the separator 11 is pulled up obliquely rightward in the direction as indicated by an arrow 'B' to peel the separator 11 off the adhesive zone 9. According to this napkin 1, the separator 11 can be peeled off the adhesive zones 9, 10 in the similar manner also by holding the location of the separator 11 adjacent the fold line 17 instead of the fold line 21.

It should be understood that the illustrated napkin 1 may be provided on a central zone in the bottom surface thereof with an additional adhesive zone serving to fix the napkin 1.

With the napkin of the invention, the separator can be peeled off both the left and right wings merely by holding any one end portion of the separator, i.e., without shifting a wearer's hand from one end portion to the other end portion of the separator as the conventional napkins have required.

What is claimed is:

1. A sanitary napkin comprising a liquid-permeable topsheet, a liquid-impermeable backsheet bonded to said topsheet, a liquid-absorbent core disposed between said topsheet and said backsheet, said napkin having transversely opposite side edges and first and second wings having upper and lower surfaces and extending outward from said transversely opposite side edges of said napkin and folded back onto said topsheet above said core respectively, and a separator having outer and inner surfaces and peelably applied to first and second adhesive zones on the lower surfaces of said first and second wings, wherein:

said separator further has first and second end portions, the first end portion being folded back onto the inner surface of said separator, the outer surface of the first end portion being peelably applied to said first adhesive zone, said second end portion being peelably applied to the adhesive zone of said second wings such that said separator can be peeled off the left and the right wings by a single hand of a user by holding and pulling one of the first and the second end portions of said separator up and away from said napkin.

2. The sanitary napkin according to claim 1, wherein the inner surface of said second end portion is peelably applied to said second adhesive zone.

3. The sanitary napkin according to claim 1, wherein said second end portion is folded back onto the inner surface of said separator, the outer surface of said second end portion being peelably applied to said second adhesive zone.

* * * * *